United States Patent
Shanklin et al.

(10) Patent No.: US 7,323,335 B2
(45) Date of Patent: *Jan. 29, 2008

(54) MUTANT FATTY ACID DESATURASE AND METHODS FOR DIRECTED MUTAGENESIS

(75) Inventors: John Shanklin, Shoreham, NY (US); Edward J. Whittle, Greenport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 344 days.

This patent is subject to a terminal disclaimer.

(21) Appl. No.: 10/822,370

(22) Filed: Apr. 12, 2004

(65) Prior Publication Data

US 2005/0005325 A1    Jan. 6, 2005

Related U.S. Application Data

(63) Continuation-in-part of application No. 10/017,145, filed on Dec. 14, 2001, now abandoned, which is a continuation-in-part of application No. 09/328,550, filed on Jun. 9, 1999, now abandoned, which is a continuation-in-part of application No. 09/233,856, filed on Jan. 19, 1999, now abandoned.

(51) Int. Cl.
*C12N 5/04* (2006.01)
*C12N 9/02* (2006.01)
*C12N 1/20* (2006.01)
*C07H 21/04* (2006.01)

(52) U.S. Cl. ............ 435/419; 435/189; 435/252.3; 435/320.1; 536/23.2

(58) Field of Classification Search ........ 435/419, 435/189, 243, 252.3, 320.1; 536/23.2
See application file for complete search history.

(56) References Cited

U.S. PATENT DOCUMENTS 5,705,391 A * 1/1998 Cahoon et al. ............ 435/419
6,100,091 A * 8/2000 Cahoon et al. ............ 435/455

OTHER PUBLICATIONS

Cahoon et al. [PNAS 94: 4872-4877, May 1997, Reference 1].*

* cited by examiner

*Primary Examiner*—Tekchand Saidha
(74) *Attorney, Agent, or Firm*—Lori-Anne Neiger

(57) ABSTRACT

The present invention relates to methods for producing fatty acid desaturase mutants having a substantially increased activity towards substrates with fewer than 18 carbon atom chains relative to an unmutagenized precursor desaturase having an 18 carbon chain length specificity, the sequences encoding the desaturases and to the desaturases that are produced by the methods. The present invention further relates to a method for altering a function of a protein, including a fatty acid desaturase, through directed mutagenesis involving identifying candidate amino acid residues, producing a library of mutants of the protein by simultaneously randomizing all amino acid candidates, and selecting for mutants which exhibit the desired alteration of function. Candidate amino acids are identified by a combination of methods. Enzymatic, binding, structural and other functions of proteins can be altered by the method.

19 Claims, 3 Drawing Sheets

```
   1  GCC TCT ACC CTC AAG TCT GGT TCT AAG GAA GTT GAG AAT CTC AAG AAG CCT TTC    54
   1   A   S   T   L   K   S   G   S   K   E   V   E   N   L   K   K   P   F     18

55  ATG CCT CCT CGG GAG GTA CAT GTT CAG GTT ACC CAT TCT ATG CCA CCC CAA AAG   108
  19   M   P   P   R   E   V   H   V   Q   V   T   H   S   M   P   P   Q   K    36

109  ATT GAG ATC TTT AAA TCC CTA GAC AAT TGG GCT GAG GAG AAC ATT CTG GTT CAT   162
  37   I   E   I   F   K   S   L   D   N   W   A   E   E   N   I   L   V   H    54

163  CTG AAG CCA GTT GAG AAA TGT TGG CAA CCG CAG GAT TTT TTG CCA GAT CCC GCC   216
  55   L   K   P   V   E   K   C   W   Q   P   Q   D   F   L   P   D   P   A    72

217  TCT GAT GGA TTT GAT GAG CAA GTC AGG GAA CTC AGG GAG AGA GCA AAG GAG ATT   270
  73   S   D   G   F   D   E   Q   V   R   E   L   R   E   R   A   K   E   I    90

271  CCT GAT GAT TAT TTT GTT GTT TTG GTT GGA GAC ATG ATA ACG GAA GAA GCC CTT   324
  91   P   D   D   Y   F   V   V   L   V   G   D   M   I   T   E   E   A   L   108

325  CCC ACT TAT CAA ACA ATG CTG AAT ACC TTG GAT GGA GTT CGG GAT GAA ACA GGT   378
 109   P   T   Y   Q   T   M   L   N   T   L   D   G   V   R   D   E   T   G   126

379  GCA AGT CCG ACG TCT TGG GCA ATT TGG ACA AGG GCA TGG ACT GCG GAA GAG AAT   432
 127   A   S   P   T   S   W   A   I   W   T   R   A   W   T   A   E   E   N   144

433  AGA CAT GGT GAC CTC CTC AAT AAG TAT CTC TAC CTA TCT GGA CGA GTG GAC ATG   486
 145   R   H   G   D   L   L   N   K   Y   L   Y   L   S   G   R   V   D   M   162

487  AGG CAA ATT GAG AAG ACA ATT CAA TAT TTG ATT GGT TCA GGA ATG GAT CCG CGG   540
 163   R   Q   I   E   K   T   I   Q   Y   L   I   G   S   G   M   D   P   R   180

541  ACA GAA AAC AGT CCA TAC CTT GGG TTC ATC TAT ACA TCA TTC CAG GAA AGG GCA   594
 181   T   E   N   S   P   Y   L   G   F   I   Y   T   S   F   Q   E   R   A   198

595  ACC TTC ATT TCT CAT GGG AAC ACT GCC CGA CAA GCC AAA GAG CAT GGA GAC ATA   648
 199   T   F   I   S   H   G   N   T   A   R   Q   A   K   E   H   G   D   I   216

649  AAG TTG GCT CAA ATA TGT GGT ACA ATT GCT GCA GAT GAG AAG CGC CAT GAG ACA   702
 217   K   L   A   Q   I   C   G   T   I   A   A   D   E   K   R   H   E   T   234

703  GCC TAC ACA AAG ATA GTG GAA AAA CTC TTT GAG ATT GAT CCT GAT GGT ACC GTT   756
 235   A   Y   T   K   I   V   E   K   L   F   E   I   D   P   D   G   T   V   252

757  TTG GCT TTT GCT GAT ATG ATG AGA AAG AAA ATT TCT ATG CCT GCA CAC TTG ATG   810
 253   L   A   F   A   D   M   M   R   K   K   I   S   M   P   A   H   L   M   270

811  TAT GAT GGC CGA GAT GAT AAT CTT TTT GAC CAC TTT TCA GCT GTT GCG CAG CGT   864
 271   Y   D   G   R   D   D   N   L   F   D   H   F   S   A   V   A   Q   R   288

865  CTT GGA GTC TAC ACA GCA AAG GAT TAT GCA GAT ATA TTG GAG TTC TTG GTG GGC   918
 289   L   G   V   Y   T   A   K   D   Y   A   D   I   L   E   F   L   V   G   306

919  AGA TGG AAG GTG GAT AAA CTA ACG GGC CTT TCA GCT GAG GGA CAA AAG GCT CAG   972
 307   R   W   K   V   D   K   L   T   G   L   S   A   E   G   Q   K   A   Q   324

973  GAC TAT GTT TGT CGG TTA CCT CCA AGA ATT AGA AGG CTG GAA GAG AGA GCT CAA  1026
 325   D   Y   V   C   R   L   P   P   R   I   R   R   L   E   E   R   A   Q   342

1027  GGA AGG GCA AAG GAA GCA CCC ACC ATG CCT TTC AGC TGG ATT TTC GAT AGG CAA  1080
 343   G   R   A   K   E   A   P   T   M   P   F   S   W   I   F   D   R   Q   360

1081  GTG AAG CTG TAG                                                           1092
 361   V   K   L   *
```

FIG. 1

MUTANT FATTY ACID DESATURASE AND METHODS FOR DIRECTED MUTAGENESIS

RELATED APPLICATIONS

The present application is a continuation-in-part of U.S. patent application Ser. No. 10/017,145 filed on Dec. 14, 2001, now abandoned which was a continuation-in-part of U.S. patent application Ser. No. 09/328,550 filed on Jun. 9, 1999, now abandoned which was a continuation-in-part of U.S. patent application Ser. No. 09/233,856 filed on Jan. 19, 1999, now abandoned.

This invention was made with Government support under contract number DE-AC02-98CH10886, awarded by the U.S. Department of Energy. The Government has certain rights in the invention.

BACKGROUND OF THE INVENTION

Fatty acid biosynthesis in higher plants has recently attracted increased interest because of the possible use of plant oils as renewable sources for reduced carbon. The diversity of fatty acid forms in wild plants is vast compared to that of crop plants. This diversity is reflected in the variations in chain length, the number and position of double bonds, and the position and occurrence of a variety of other functional groups in the fatty acids of wild plants.

In plants, fatty acid biosynthesis occurs in the chloroplasts of green tissue or in the plastids of non-photosynthetic tissues. The primary products in most plants are acyl carrier protein (ACP) esters of the saturated palmitic (palmitoyl-ACP) and/or stearic (stearoyl-ACP) acids, palmitic acid having a 16 carbon atom chain length and stearic acid having an 18 carbon atom chain length. Two types of desaturase molecules are involved in the production of monounsaturated fatty acids (monoenes), soluble, and integral membrane proteins. Desaturases are specific for a particular substrate carbon atom chain length (chain length specificity) and introduce the double bond between specific carbon atoms in the chain (double bond positional specificity) by counting from the carboxyl end of the fatty acid. For instance, the castor $\Delta^9$-18:0 desaturase is specific for stearoyl-ACP, and introduces a double bond between carbon atoms 9 and 10.

The introduction of non-native desaturase isoforms having unique characteristic chain length and double bond positional specificities into agricultural crops offers a way to manipulate the content, physical properties and commercial uses of plant-produced oils. Unfortunately, the introduction of non-native acyl-ACP desaturase isoforms into agricultural crop plants has yet to lead to the efficient production of unusual or uniquely useful monoenes by agricultural crop plants. An alternative way in which to accomplish the manipulation of the content, physical properties and commercial uses of oilseed crops would be through the introduction of a native desaturase which had been manipulated in such a way as to alter its chain length and/or double bond positional specificities.

As the genes encoding more desaturase enzymes are identified it is becoming apparent that many of the different activities are derived from relatively few common archetypes encoding the soluble and membrane classes of desaturases.

Molecular modeling and X-ray crystallographic studies of soluble acyl-ACP desaturases have identified amino acid residues within the substrate binding channel which are in very close proximity to the fatty acid substrate. Such residues are referred to as "contact residues". That earlier research demonstrated that certain modifications of one or more contact residues and modification of some non-contact residues can alter the in vitro chain-length and double bond positional specificities of acyl-ACP desaturases (Cahoon, et al. Proc. Natl. Acad. Sci. USA (1997) 94:4872-4877 and Cahoon, et al. U.S. Pat. Nos. 5,705,391, 5,888,790 and 6,100,091). Those studies were carried out using predictions formulated from the three dimensional structure of the castor $\Delta^9$-18:0 acyl-ACP desaturase in combination with alignment of its sequence with that of a $\Delta^6$-16:0 acyl-ACP desaturase as well as with the sequences of other 18:0 desaturases. The studies examined the effects of replacing specific contact and non-contact amino acid residues of the $\Delta^6$-16:0 desaturase with various amino acid residues in cognate positions in the $\Delta^9$-18:0 desaturase on the in vitro substrate chain length and double bond positional specificities of the 16:0 desaturase. The studies demonstrated that substituting a major portion of the substrate binding channel of a $\Delta^9$-18:0 desaturase into the homologous position of a $\Delta^6$-16:0 desaturase converted its in vitro specificity to that of a $\Delta^9$-18:0 desaturase. This could also be accomplished by replacing one contact and four non-contact amino acids of the $\Delta^6$-16:0 desaturase with five amino acids of the $\Delta^9$-18:0 desaturase which occupy homologous positions. It was also shown that substituting bulky contact amino acid residues (isoleucine for proline at position 179 and phenylalanine for leucine at position 118) into the substrate binding channel of the $\Delta^9$-18:0 desaturase increased its preference for the 16:0-ACP substrate such that the in vitro 16:0-ACP activity became slightly more than two-fold greater than its remaining 18:0-ACP activity.

The ability to manipulate the chain length and double bond position specificities of desaturases has great potential with regard to generation and use of mutated native desaturases in the production of commercially useful products, such as vegetable oils rich in monounsaturated fatty acids. Such vegetable oils are important in human nutrition. In addition, because a double bond in an otherwise saturated carbon chain is readily susceptible to chemical modification, fatty acid chains having double bonds in unique positions produced by crop plants can be useful raw materials for industrial processes.

The earlier studies making use of molecular modeling and crystallographic data, while successful, was extremely time consuming and the in vitro activity of the altered enzymes was not directly correlated to the in vivo specificities of the altered enzymes. Those studies pointed out a need for a simplified and general method for readily producing mutants of desaturases which have altered and desirable chain length and double bond positional specificities.

SUMMARY OF THE INVENTION

The present invention relates to a simple and general method for identifying and producing a mutant of a fatty acid desaturase, the original desaturase having an 18 carbon atom chain length substrate specificity, the mutant produced having substantially increased activity relative to the original desaturase towards fatty acid substrates with chains containing fewer than 18 carbons. The method involves inducing one or more mutations in the nucleic acid sequence encoding the original desaturase, transforming the mutated nucleic acid sequence under conditions for expression into a cell which normally requires a growth medium that is supplemented with unsaturated fatty acids in order to proliferate (i.e., an unsaturated fatty acid auxotroph cell), and then selecting for recipient cells which have received a mutant fatty acid desaturase with a specificity for shorter carbon atom chain length substrates.

In a preferred embodiment, the mutated nucleic acid sequences are transformed into an *E. coli* unsaturated fatty acid auxotroph designated MH13. The cells are then grown in the absence of added unsaturated fatty acids to select for recipient MH13 cells which express mutated enzymes which are capable of producing sufficient unsaturated fatty acids in the cell to support growth, thereby overcoming the auxotrophy.

Another aspect of the present invention includes the DNA sequences encoding the mutant enzymes and the mutants which are produced. Mutants of castor $\Delta^9$-18:0-ACP desaturase produced by the method arise from amino acid substitutions at specific residues. These mutants each have altered substrate chain length specificity, of 16- or fewer carbon atoms. Other embodiments of the present invention encompass the expression of the mutant desaturase molecules in individual cells and also in transgenic plants, for the production of specific fatty acid products.

Another aspect of the present invention is a method for specifically altering a function of a protein through directed mutagenesis. The method involves identifying candidate amino acid positions of the protein which, when mutated, are predicted to alter the function. A library of mutant sequences produced by simultaneous combinatorial randomization of the codon at each candidate position, in combination with randomization of every other candidate position is generated, and mutant encoded proteins which exhibit the desired specific alteration of function are identified from the library by selection. In a preferred embodiment, candidate amino acid positions are identified by a combination of methods, some examples being random mutagenesis, structural analysis of the protein, and sequence analysis of the protein. Examples of functions which the method can be used to alter include enzymatic functions, substrate specificity, binding functions, and structural functions. The method of the present invention is compared to the method of random mutagenesis in alteration of castor $\Delta^9$-18:0-ACP desaturase substrate chain length specificity.

BRIEF DESCRIPTION OF THE DRAWINGS

FIG. 1 lists the amino acid sequence of mature castor enzyme (SEQ ID NO: 1), and the corresponding nucleic acid coding sequence (SEQ ID NO: 2).

DETAILED DESCRIPTION OF THE INVENTION

Figure 2:
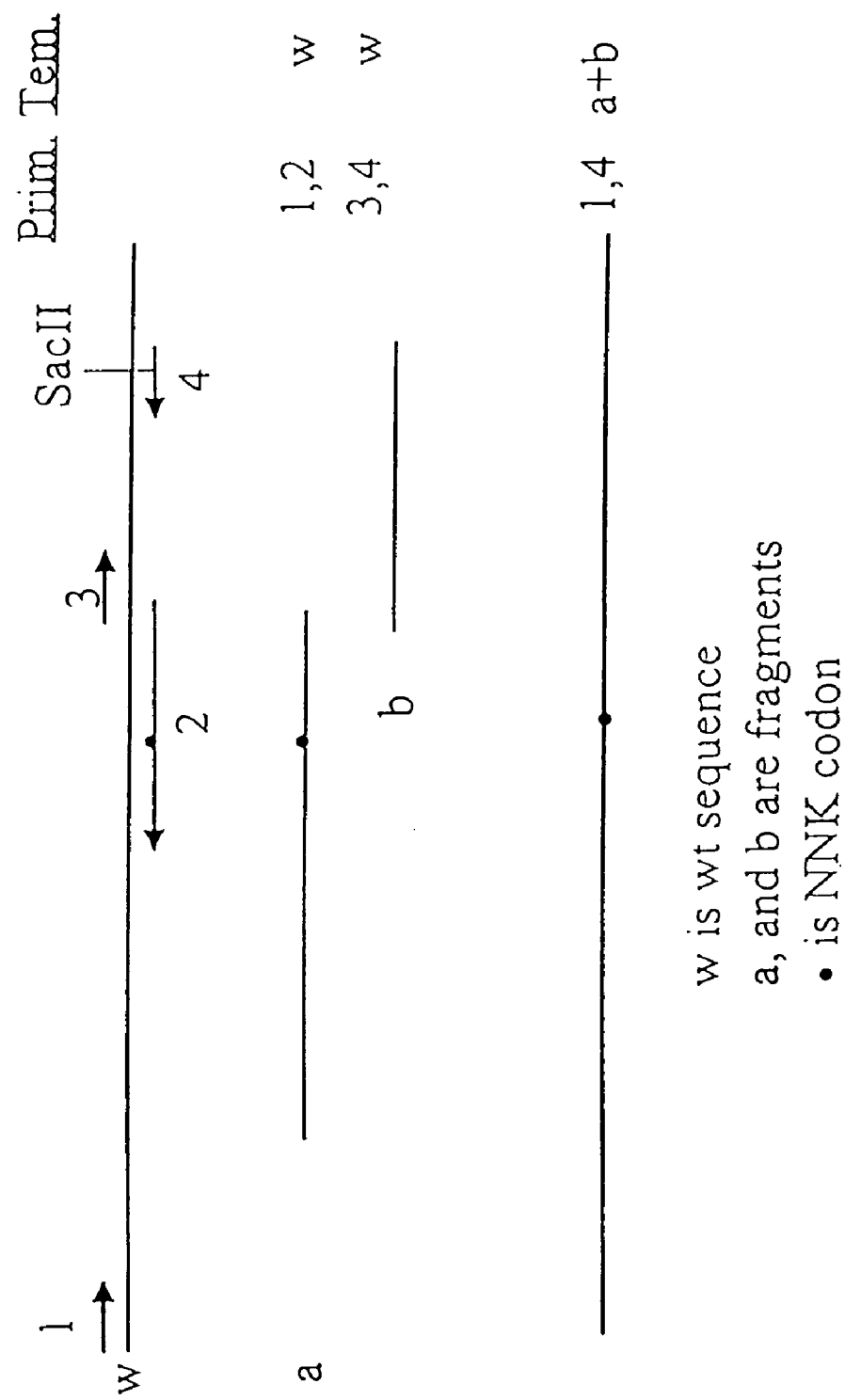
FIG. 2 is a diagram illustrating the primers used for full positional randomization of site 117 of castor $\Delta^9$-18:0-ACP desaturase.

The present invention is based on the use of a bacterial selection system for the selection of mutant desaturase molecules which have 18-carbon atom chain length substrate specificities prior to the introduction of the mutation and which have a 16 or fewer carbon atom chain length substrate specificity of as a result of the mutation. A preferred bacterial strain used in the selection system, *E. coli* MH13, is an unsaturated fatty acid auxotroph. MH13 normally requires a growth medium that is supplemented with unsaturated fatty acids in order to proliferate. Previous research (Cahoon, et al., (1996) J. Bacteriology 178:936-939 and Thompson, et al. (1991) Proc. Natl. Acad. Sci. USA 88:2578-2582) demonstrated that although 14:0 and 16:0 acyl-ACP desaturases were able to use in vivo pools of acyl-ACPs in *E. coli* to produce monounsaturated fatty acids, $\Delta^9$-18:0 acyl-ACP desaturases do not generate detectable amounts of monounsaturated fatty acids when expressed in *E. coli*. Thus, due to the substrate pools of saturated fatty acid substrates in *E. coli*, the $\Delta^9$-18:0 desaturase enzymes are not sufficiently active in the *E. coli* host cell and are thus not able to complement the deficiency in unsaturated fatty acid auxotrophs such as *E. coli* MH13. Desaturase enzymes which specifically utilize 18-carbon chain length substrates cannot complement the auxotrophy due to the low levels of such 18-carbon chain length substrates in the bacterial cell. However, introduction of a functional desaturase enzyme which has substantial activity towards fatty acid substrates with chains containing 16 or fewer carbons will complement this auxotrophy, allowing for the growth and proliferation of the bacteria in the absence of supplemental unsaturated fatty acids. These observations have been exploited as a selection system for identifying mutants of an 18-carbon specific fatty acid desaturase which have a substantially increased activity towards fatty acid substrates with chains containing 16 carbons or 14 carbons. While *E. coli* MH13 is a preferred host cell, one of skill in the art will recognize that other host cell types may be employed.

The present invention provides for a method of producing a mutant of a fatty acid desaturase, the mutant being characterized as having a specificity for shorter chain length fatty acid substrates compared to the original fatty acid desaturase. The method requires nucleic acid sequences encoding a fatty acid desaturase with 18 carbon atom chain length substrate specificity. To produce the mutant, mutations are induced in the nucleic acid sequence encoding the fatty acid desaturase. The mutated nucleic acid sequence is then transformed into the MH13 *E. coli* cells under conditions appropriate for expression of the mutated sequence. The transformed MH13 *E. coli* cells are then selected for the ability to grow in the absence of supplemental unsaturated fatty acids. Survival of a transformed MH13 *E. coli* indicates the acquisition of a mutant fatty acid desaturase which complements the fatty acid auxotrophy of MH13 because of its altered chain length specificity.

A mutant fatty acid desaturase identified by the above selection assay has a substantial increase in the activity towards fatty acid substrates with chains containing fewer than 18 carbons, relative to the original desaturase. A substantial increase in substrate specificity with respect to the original desaturase is one that produces sufficient accumulation of unsaturated fatty acids, which results from desaturation by the mutant desaturase, within an unsaturated fatty acid auxotroph host organism so as to support growth and proliferation of the host organism. Substantial increase in activity sufficient to support growth of the auxotroph host is at least three-fold higher than that of the non-mutagenized precursor desaturase. In a preferred embodiment, the increase in activity of the mutant desaturase is at least ten-fold higher than the non-mutagenized precursor desaturase.

The Exemplification section below details experiments where the method was used to identify mutants of castor $\Delta^9$-18:0-ACP desaturase with modified substrate specificities. One of skill in the art will recognize that the method is suitable for producing mutants of any fatty acid desaturase which has an 18 carbon atom chain length substrate specificity prior to mutagenesis. To do so requires only a nucleic acid sequence for the desaturase. Expression of the nucleic acid sequence results in the production of a mature fatty acid desaturase, and following mutagenesis of the nucleic acid sequence, those sequences which are mutated to cause the alteration in the chain length specificity of enzyme will be expressed and identified through the selection procedure.

It is possible that reintroduction of a mutant desaturase into the cell or plant from which the desaturase gene was originally taken may result in more productive generation the desirable shorter monounsaturated fatty acid compared to introduction of a mutant desaturase developed from a different cell or plant. In addition to castor, it would be useful to produce mutant desaturases from a variety of plants, including brassica, sunflower, yellow lupine, cotton, coriander, maize, sesame, rice, flax, safflower, avocado and cucumber.

The nucleic acid sequences having silent mutations which do not affect the amino acid sequence of the translated product would not be identified in the selection procedure. Nucleic acid sequences encoding a functional fatty acid desaturase, whose amino acid sequence varies from wild type, for example with conservative amino acid substitutions that do not affect function in regard to carbon chain length substrate specificity would also not be identified in the selection procedure. However, such mutated desaturases may be desirable when incorporating several different functional mutations into one mutant.

In preferred embodiments, the fatty acid desaturase is a plant fatty acid desaturase. There are two types of plant fatty acid desaturases, soluble (acyl-ACP desaturases), and integral membrane (acyl lipid desaturases), both of which are suitable for use in the present invention.

In one embodiment, the MH13 E. coli also express an exogenous plant ferredoxin. This can be accomplished by introduction of an expression vector containing sequences which encode plant ferredoxin (e.g. Arabaena vegetative ferredoxin), and the application of selective pressure to the resulting bacteria. The presence of plant ferredoxin, the redox partner of the plant desaturases, facilitates the function of the plant desaturase in E. coli. The presence of plant ferredoxin in the selection system allows for the selection of mutants with low specific activities towards fatty acids with 16 or fewer carbon atoms. Mutants which complement MH13 in the absence of plant ferredoxin are expected to have comparatively higher specific activities toward the shorter fatty acid substrates (Cahoon, et al. (1996)).

The selection system described above is most appropriate for use in selecting mutants with the desired substrate specificity from a heterogeneous population of mutant fatty acid desaturase molecules. By transforming a population of mutated nucleic acid sequences into the auxotroph host cells, entire libraries of mutants can be screened for the ability to complement the MH13 auxotrophy.

Any type of mutation which has the potential to result in a modified fatty acid desaturase protein product can be induced in the nucleic acid sequences. Logic based approaches of introducing amino acid substitutions into residues which interact with substrate are sound but can be very labor intensive and are mainly suited to cases in which structural information is available. Such methods have been successfully employed for modifying the chain length specificity of soluble desaturases, and for the introduction of double-bond versus hydroxyl group for the membrane class of enzymes (Cahoon et al., (1997); Shanklin, et al. (1998) Annu. Rev. Plant Physiol. Plant Mol. Biol. 49:611-641).

Experiments described in the Exemplification section which follows make use of a variety of mutagenesis approaches. These experiments describe utilization of random mutagenesis, which has the potential to identify amino acids involved in substrate specificity. The use of random mutagenesis is perhaps the most powerful method because it does not rely on assumptions about which residues are important, assumptions which are based on structural information. This method has the ability to identify substitution mutations at positions which are amino acid contact residues (positions which are located nearest the substrate within the binding channel) and also positions which affect the substrate specificity without directly contacting the substrate (Cahoon et al., (1997)). However, random mutagenesis cannot produce fully randomized amino acids at most positions because of the degeneracy of the code.

Directed mutagenesis in the form of single point randomization, however, can be used to fully randomize any amino acid. In the most basic approach, directed mutagenesis is used in the experiments to individually randomize the amino acid at one specific position in the enzyme at a time (single point randomization), which position had been identified by the more laborious logic based approaches or by the random mutagenesis approach.

In a more powerful approach, site directed mutagenesis is used to specifically and simultaneously target a set of codons to randomize amino acids at specific positions within the protein product (combinatorial full positional randomization).

Once mutated, the nucleic acid sequences are transformed into the MH13 cells. Transformation is preferably accomplished by electroporation, but alternative methods known to one of skill in the art can also be used.

Following transformation, the cells are selected for the presence of the mutant fatty acid desaturase. This is accomplished by growth on selective media (e.g. media lacking exogenously supplied unsaturated fatty acids). The media can be either solid or liquid. Using several rounds of selection, and/or varying or augmenting the selective pressures involved is also useful in increasing the number of mutants identified by the method.

The present invention is useful in the engineering of desaturase proteins with characteristic substrate chain length preferences. Such isoforms, when introduced into cells or organisms (e.g. agricultural crops) can be used to manipulate the physical properties and commercial uses of conventional plant oils. Cells and organisms which express these engineered desaturases are useful in the production of commercially useful products, such as vegetable oils rich in monounsaturated fatty acids, which have many potential uses, for example in human nutrition or as industrial chemicals.

The Exemplification section below details experiments where the above described method was used to identify mutants of castor $\Delta^9$-18:0-ACP desaturase which have modified substrate specificities. Mutations in the coding region which result in amino acid substitutions at position 114, 117, 118, 179, 181, or 188, and combined substitutions at positions 114 and 188 as well as 117 and 188 and combined substitutions at all six positions, are described, along with the resulting altered specificity of these mutant proteins as compared to wild type. Mutations in the coding region of castor $\Delta^9$-18:0-ACP desaturase which produce a combination of amino acid substitutions at all six positions were identified by combinatorial full positional randomization, including the mutant proteins encoded being referred to as com2, com3, com4, com9, com10 and com25. Table 4 lists the amino acid substitutions and the specific activities of these mutant proteins for the different substrates.

All six mutant proteins listed in Table 4 have the amino acid substitution T117R and five of the six have the double substitution, T117R with G188L, in combination with various substitutions at the remaining four positions. The fact that these two mutations appear to be the optimal changes at their respective positions for increasing specificity for shorter fatty acid substrates, suggests that they may be the primary determinants for altering chain length specificity. The observation that several other mutants containing this pair of mutations have lower specific activity suggests that the combination of mutations at the remaining four (or five in the case of com2 versus com25) randomized sites can also affect the specific activity of the mutants.

By itself, the single T117R mutation, which is conserved for all six combinatorial mutants, is insufficient to cause a substantial increase in activity with shorter fatty acid substrates (see Table 2). In combination with the other substitutions found in the mutants reported in Table 4, however, the substrate specificity of the desaturase is profoundly altered. Interestingly, the in vitro activity of com25 was found to be quite variable, yet when the mutant desaturase was expressed in A. thaliana, the plant seed accumulated more 16:1 oil than did plants expressing com2. It is possible that some combinations of substitutions result in an enzyme that is variably stable when produced and isolated by recombinant methods but which is stable when the enzyme is produced in situ in a plant or other host cell. These results suggest that the change T117R in combination with a variety of changes at positions 188, 181, 179, 118 and 114 can yield mutant enzymes that differ from one another in their in vitro versus their in vivo properties.

Another aspect of the present invention is a mutant castor $\Delta^9$-18:0-ACP desaturase which has a subset of the amino acid substitutions of a mutant protein listed in Table 4. Such a mutant is expected to also have altered activity towards the different substrates. The present invention encompasses mutant castor $\Delta^9$-18:0-ACP desaturase proteins which have between 1 and 6 of the amino acid substitutions of the com2 and com25 mutants, in any possible combination. In a preferred embodiment, the combination includes at least three of the amino acid substitutions of the com2 or com25 mutants. Preferably two of these amino acid substitutions are T117R and G188L. In addition, the present invention is intended to encompass mutant $\Delta^9$-18:0-ACP desaturase proteins which have between 1 and 6 of the amino acid substitutions of the com3 mutant, the com4 mutant, the com9 mutant, or the com10 mutant, respectively, in any possible combination. In a preferred embodiment, the combination includes at least three of the amino acid substitutions, of the mutant. Preferably two of these substitutions are T117R and G188L. Also included in the present invention are mutants which have the above listed amino acid substitutions, and combinations thereof, in combination with any other amino acid substitutions, insertions or deletions. These additional substitutions, insertions or deletion, may be silent (e.g. do not affect function of the enzyme) or may further alter enzyme function.

The above listed amino acid substitutions made at the analogous positions in other ACP-desaturases, especially in 18:0-ACP desaturases, and preferably in $\Delta^9$-18:0-ACP desaturases, are predicted to have the analogous effects on substrate specificity in these proteins as in the disclosed castor desaturase mutants. Such candidate desaturase genes could be isolated from such sources as brassica, sunflower, yellow lupine, cotton, coriander, maize, sesame, rice, flax, safflower, avocado and cucumber.

Nucleic acid sequences which encode the mutant proteins described above, can be inserted into a DNA expression vector, which can then be used to express the mutant proteins in cells. Expression vectors which function in either or both prokaryotic and eukaryotic cells exist and are known to those of skill in the art. The appropriate expression vectors are introduced into either prokaryotic cells, (e.g. bacteria) or eukaryotic cells (e.g. animal cells or plant cells) under conditions appropriate for expression of their coding sequences. Plant cells which express the mutant proteins can be used to produce transgenic plants which express the mutant proteins, and which produce the corresponding fatty acid products of the desaturases.

Another aspect of the present invention is a method for specifically altering a function of a protein through directed mutagenesis. Upon determination of the specific function which is to be altered, candidate amino acid positions of the protein, which are predicted to alter the function when mutated, are identified. Several methods for identifying candidate positions are described below. A library of mutant sequences encoding the protein are generated by randomization of the amino acid encoded at each candidate position, in combination with randomization of every other candidate position within each mutant. This is generally accomplished by generating a library of mutant nucleic acid sequences which encode the mutant proteins through simultaneous randomization of the codon at every candidate position. Mutant proteins, encoded by the mutated nucleic acid sequences, exhibiting the desired alteration of function are then identified from the library.

A wide variety of functions are performed by proteins. Some proteins function as enzymes which catalyze reactions (e.g. catabolic, anabolic), some proteins function as binding proteins (e.g. ligand binding receptors, antibodies, adapter proteins), some proteins function as structural proteins (e.g. extracellular matrix proteins). The present invention is useful for altering any given function of any given protein. Because many proteins have more than one function, the specific function which is to be altered must first be determined. Often the functions of a multifunctional protein are independent of one another, allowing one function to be altered without affecting the other function(s) of the protein. In other cases, the functions are interlinked or interdependent, making alteration of a single function more complex. Alteration of a function is broadly defined herein as including any directed change in the function. Such changes include, without limitation, optimization of a function, (e.g. increasing the specific activity of an enzyme, increasing the binding affinity of a binding protein, increasing the integrity or stability of a protein's structure), redirection of a functional property of a protein (e.g. modifying the substrate specificity of an enzyme, modifying the binding specificity of a binding protein, modifying a structural component of a protein), and reduction (e.g. abolishing) of a function. Complete alteration of a designated function may necessarily be achieved in stages through sequential alteration of individual components of the function, producing a series of intermediate mutants, the entire process culminating in the generation of a final optimal mutant. Therefore, the process of altering a function of a protein as described herein, is intended to include optimizing, redirecting, or reducing a function of a previously altered protein.

Candidate positions include the positions of amino acids of the wild type protein which are involved (either directly or indirectly) in the function. Importantly, an indication of involvement in the function is all that is required for selection of candidate positions. The direction an individual mutation has or is expected to have on the function is unimportant in the identification of candidate positions. For instance, residues which, when mutated individually, result in a decrease of the function, may be identified as candidates. Examples of amino acids which are directly involved with function include, without limitation, residues which make contact with other molecules involved in the function (e.g. substrate or ligand), and also residues which line or define binding sites. Examples of amino acids which have indirect involvement include, without limitation, residues which influence those directly involved residues, such as residues adjacent or near directly involved residues. Proximity need not be limited to primary sequence, but may result from secondary or tertiary structure relationships. In addition, residues may be located near directly involved residues due to the formation of inter- or intra-molecular complexes. The influence that indirectly involved amino acids can have may be steric effects, chemical effects, or a combination of effects. Indirectly involved amino acids also include residues which participate in defining an element of the protein structure which is crucial for the function (e.g. the necessary conformation of a protein).

Candidate positions also include positions of amino acids which are not significantly involved (directly or indirectly) in the function of the wild type protein, but which assume a role (direct or indirect) in function through mutagenesis. The term wild type is used herein to refer to the original sequence of a protein prior to mutagenesis, the term being inclusive of previously altered sequences. Mutagenesis which confers a role in function to a previously uninvolved residue commonly involves the substitution of another amino acid at that particular position. However, a new involvement in function may also be conferred to a position by mutagenesis at another position.

The more information one has regarding the protein, the function of the protein which is to be altered, and the residues which participate in the function, the more productively one can go about altering the function.

Candidate amino acid positions of the protein are identified by any number of means. Without limitation, such means include, random mutagenesis of the nucleic acid sequences encoding the protein, structural analysis of the protein, and sequence analysis of the protein, often coupled with comparison to related proteins. Methods for identification of candidate positions may be performed with the naturally occurring protein, or alternatively with a mutant version of the protein. In addition, analysis of related proteins (e.g. sequence analysis, structural analysis, mutagenesis) may indicate analogous candidate positions within the protein of interest which are likely involved in the function to be altered. The term related proteins as used herein includes different isomers of a protein, different phenotypes of a protein (e.g. naturally occurring mutants of the same protein), and any other proteins or fragments thereof which have significant homology to the protein whose specific function is to be altered.

Random mutagenesis coupled with screening for loss or change of function mutants can identify candidate amino acid positions which are crucial for function of the wild type protein. Random mutagenesis coupled with screening for gain or enhancement of function mutants can identify these crucial positions as well as positions which only minimally participate in wild type function, but have gained an increased role through mutagenesis.

Structural analysis of a protein is also a very powerful tool with which to identify candidate residues. Structural information can be obtained from X-ray crystallography, or from other methods such as nuclear magnetic resonance. Often the structure of a protein performing of the function (e.g. an enzyme bound to substrate or an inhibitor, or a binding protein bound to ligand) provides a significant amount of information regarding the amino acid positions involved in the function.

Preferably, a combination of methods are employed to identify candidate amino acid positions. In a preferred embodiment, all available means are employed to ensure identification of as many candidate positions as possible.

Once the candidate positions are identified, libraries of mutated sequences encoding the mutant proteins are developed. Where this method of substituting 1 of the 20 possible amino acids at one specific position within a protein is referred to herein as single point randomization of the amino acid.

Simultaneous randomization of the amino acid encoded at each and every candidate codon within an individual particular protein is referred to herein as combinatorial full positional randomization or variously full positional randomization. Mutant proteins resulting from combinatorial full positional randomization are most easily produced by generating a nucleic acid library of mutated coding sequences, which have 1 of 20 possible amino acid encoded at every candidate position and then selecting the mutated sequences that encode proteins having the desired altered activity. Because this type of mutagenesis allows for the insertion of a codon for the wild type residue, as well as the other 19 residues, at each candidate position, this produces the widest possible variety of mutation combinations. Combinatorial full positional randomization of codons can be accomplished by a variety of methods. One such method is the use of overlap-extension PCR to replace all codons for candidate position amino acids with NNK or NNN. The process of overlap-extension PCR has been used to simultaneously introduce at least nine independent mutations into a particular coding sequence.

In another embodiment, a subset of one or more of the candidate positions are incompletely randomized, while the other candidate positions are fully randomized. That is to say, fewer than the 20 possible amino acids are introduced at one or more designated candidate positions, to more specifically direct the mutagenesis. This is accomplished by randomly replacing the subset of candidate position codons of the nucleic acid sequence which encode the protein, with codons that encode the desired subset of amino acids, while introducing codons which encode all 20 amino acids at the other candidate positions.

Once the library is generated, mutant proteins which exhibit the desired altered function are identified. This is most efficiently accomplished by using a functional selection process. The mutated nucleic acid sequences are expressed individually, preferably by individual introduction into a single celled organism under conditions appropriate for expression. Once expressed, the mutant proteins which exhibit the desired function may be selected by their function (e.g. a complementation assay). Alternatively, populations of mutants generated can be screened for the desired altered function (e.g. by a rapid screening process). Each mutant generated can also be individually assayed for the desired altered function.

Experiments detailed in the Exemplification section which follows were performed to modify the substrate specificity of castor $\Delta^9$-18:0-ACP desaturase. Structural analysis of the protein was combined with random mutagenesis to identify candidate residues.

Random mutagenesis was used to identify candidate residues of the desaturase by a functional assay. Theoretically, this method of identification has the potential to identify residues which may or may not line the substrate binding cavity, they are simply identified by a functional assay, thus this method of identifying residues likely to participate in function is applicable to both enzymes for which a structure is known, and enzymes for which a structure is unknown. All relevant knowledge should be included in compiling the list of candidate amino acid positions to be randomized.

One distinguishing feature of the present invention is that combinatorial full positional randomization is performed simultaneously on all candidate positions which are identified. Previous approaches to directed mutagenesis to specifically alter a function of a protein have used a multistep approach, where one residue is mutated, the mutant is characterized, and then that mutant is subjected to another round of single position mutagenesis. This standard approach results in each subsequently produced mutant carrying over specific mutations from the last mutant product. Thus, each subsequent mutant identified is necessarily constrained by properties inherited from the mutant from which it is generated, thus limiting the direction the mutagenesis may take to achieve the desired function. By eliminating this limitation, the method of the present invention generates a wider variety of mutants which demonstrate the desired activity, from which one can select an optimal mutant.

EXEMPLIFICATION

Section I: Preliminary Studies

A mutagenesis and selection approach was employed to identify amino acid substitution mutations in plant fatty acid desaturases which modify substrate specificity. Acyl-ACP desaturases are functionally active when expressed in *E. coli*. $\Delta^9$-18:0-ACP desaturases are unable to alter the fatty acid profile of *E. coli* due to a lack of appropriate substrate (Thompson et al., (1991)). However, desaturases with 16:0 or 14:0 specificity were shown to alter the fatty acid profile of *E. coli* (Cahoon, et al. (1996)). Thus, 18:0 desaturases cannot complement the *E. coli* mutant MH13, an unsaturated fatty acid auxotroph, but desaturases with specificities with 16 or fewer carbons are able to complement this auxotrophy. Thus, the MH13 *E. coli* strain was used to select for mutants of an 18-carbon desaturase which can utilize 16- or 14-carbon substrates in a complementation assay.

To facilitate the function of a plant acyl-ACP desaturase in *E. coli*, an expression vector containing the gene for plant-type ferredoxin, the redox partner of the plant desaturase, was transformed into the MH13 *E. coli* and maintained under selective pressure. These cells, MH13(pACYC/LacAnFd) were used in the following experiments.

The nucleic acid sequence for castor $\Delta^9$-18:0-ACP desaturase was subjected to one of two types of mutagenesis, site directed or random mutagenesis, prior to introduction into the MH13 cells. PCR was used in site directed mutagenesis to randomize a targeted codon corresponding to a specified residue in the amino acid sequence of the castor $\Delta^9$-18:0-ACP desaturase. Target codons corresponding to Met 114, Leu 118, Pro 179, and Gly 188 were each subjected to independent randomization (single point randomization). Previous studies (Cahoon, et al. (1997)) had indicated that these residues are located adjacent to the substrate binding cavity and that replacing some of those amino acids in the T. alata $\Delta^6$-16:0 desaturase or in the castor $\Delta^9$-18:0 desaturase with bulkier or less bulky amino acids could affect substrate specificity in vitro. The methods of the present invention allowed for an unbiased substitution of all 20 amino acids into these positions but required that the mutation affect the in vivo substrate specificity of the desaturase. The mutagenesis reactions yielded four populations, each one comprising a library of coding sequences with substitution mutations consisting of all 20 potential amino acids at the designated mutation site.

To examine whether mutations in additional contact and/or non-contact residues could alter the in vivo substrate specificity of the castor $\Delta^9$-18:0-ACP desaturase, a totally unbiased approach using random mutagenesis by single gene DNA shuffling was performed on the sequences encoding castor $\Delta^9$-18:0-ACP desaturase.

MH13(pACYC/LacAnFd) were transformed with the resulting libraries of mutated 18:0-ACP desaturase, under conditions appropriate for expression, and then selected for expression of a mutant with the ability to complement the unsaturated fatty acid auxotrophy, by growth in the absence of supplemental unsaturated fatty acid. To confer survival under the selective conditions, a mutant desaturase would necessarily have an altered substrate chain length specificity of 16, 14 or fewer carbons. The selection for site directed mutants was performed in either liquid media or on agar plates. The selection for randomly generated mutants was performed on agar plates. Growth in liquid media involved several rounds of dilution and re-growth to enrich for mutations that resulted in the best complementation.

In a variation on the single point randomization, mutants were selected from a library encoding all 400 possible combinations of amino acids at position 188 and 114, two adjacent contact residues within the substrate binding channel. This was achieved by excising a restriction fragment from the open reading frame of the library encoding all possible amino acids at position 188 and inserting this fragment into the equivalent plasmid population randomized for position 114. Using this method, the double mutant M114I-G188L was identified in the selection procedure.

The coding sequences of selected desaturases were sequenced to identify the specific mutations which conferred complementation of the fatty acid auxotrophy. The substrate specificities of the identified mutants were determined by in vitro enzyme assays (Cahoon et al., (1997)). Table 1 lists the identified mutations and the altered chain length substrate specificity conferred.

The designated amino acid positions in Table 1 correspond to the mature castor enzyme as defined in Lindqvist et al., EMBO J. 15: 4081-4092 (1996), the sequence of which is listed in FIG. 1 (SEQ ID NO: 1).

TABLE 1

| | Mutagenesis Method | | Fold change in specificity with respect to wt | |
|---|---|---|---|---|
| Position | SPR | RM | 16:18 | 14:18 |
| Met 114 | Ile (16) | Ile (16) | 6 | |
| Met 114 | Phe (14)/ Tyr (14) | | Phe 7 | 490 |
| Thr 117 | | Ile (16) | not determined | |
| Leu 118 | Phe (16)/ Tyr (16) | Phe (16)/ Met (16) | Tyr 130 | |
| Pro 179 | Ile (16) | Leu (14) | 20 | |

TABLE 1-continued

| Position | Mutagenesis Method | | Fold change in specificity with respect to wt | |
|---|---|---|---|---|
| | SPR | RM | 16:18 | 14:18 |
| Thr 181 | | Ile (16) | not determined | |
| Gly 188 | Leu (16) | | 740 | |
| M114/G188 | M114I/ G188L (16) | | 1410 | |

Mutations obtained by mutagenesis/selection. Numbers in parentheses represent the chain length specificity that is most enhanced with respect to the wt castor $\Delta^9$-18:0 desaturase activity. Shown are also the fold change in specificity ratios where known. For instance, if the activity with respect to 16 carbon was increased by 10-fold, and the activity with respect to 18:0 was decreased by 5-fold, the "Fold change in specificity with respect to wt" for 16:18 would be 50.
SPR = single point randomization;
RM = random mutagenesis While the use of structure-guided (i.e., directed) mutagenesis of residues M114, L118, P179 and G188 was effective for the identification of seven mutants with substrate specificities of 16 or fewer carbon fatty acids, the method relied on the appropriate choice of target residues for mutagenesis. It is well documented that residues that affect substrate specificity fall into two broad classes, direct and indirect. Thus, random mutagenesis selection provides a bias-free method for the identification of changes that result in increased specificity for shorter acyl chains. Through random mutagenesis and selection of the present invention, five amino acid positions were identified, three at sites that were also targets for the structure-guided mutagenesis and two new sites, T117 and T181.

The naturally occurring 16:0-ACP desaturases from Milkweed and Doxantha have very poor activities when assayed in vitro (31 and 3 nM/min/mg, respectively). However, the selected mutant G188L has an activity of 175 nM/min/mg, much closer to that of the parental wild type castor $\Delta^9$-18:0-ACP desaturase with its 18:0-ACP substrate.

To test whether the altered enzymes identified in the selection assay would result in the accumulation of unusual fatty acids when expressed in plants, the G188L mutant was introduced into *Arabidopsis thaliana* (fab1 background) using a napin promoter to drive expression. The first generation of G188L transgenics (T1) produced seeds which contained approximately 10% of fatty acids modified by the introduced desaturase. Because T1 seeds are heterozygous it is anticipated the levels of desired fatty acids will increase in the homozygous T2 plants. These results suggest that mutants derived from castor $\Delta^9$-18:0-ACP desaturase may be useful for future metabolic engineering of oil crops.

Materials and Methods for Section I

Cell strains. The *E. coli* unsaturated fatty acid auxotroph MH13 mutant of *E. coli* K12 (Henry, M. F., Ph. D. Thesis, University of Illinois, Urbana-Champaign (1992)) is a fadR::Tn5 mutant of cell strain DC308 (Clark et al., (1983) Biochemistry 22:5897-5902) which was constructed by phage P1 transduction from strain RS3069 (Simons et al., (1980) J. Bacteriol. 142:621-632). MH13 requires a medium supplemented with unsaturated fatty acids at all growth temperatures due to a temperature-sensitive lesion in fabA and transposon disruption of fadR. An XbaI/EcoRI fragment from a pET9d expression plasmid containing the coding sequence of Anabaena vegetative ferredoxin (Fd) (Cheng et al., (1995) Arch. Biochem. Biophys. 316:619-634) was inserted into the corresponding sites of pLac3d to generate the plasmid pLacAnFd. pLac3d is analogous to pET3d except that the T7 RNA polymerase promoter has been replaced with the lacUV5 promoter of *E. coli* RNA polymerase as described previously (Cahoon et al., (1996)). A BglII/HindIII fragment from pLacAnFd was then inserted into the BamHI/HindIII sites of pACYC184. This construct (pACYC/LacAnFd) was then introduced into MH13 cells by electroporation.

Complementation Analysis/Selection. The *E. coli* MH13 strain harboring pACYC/LacAnFd was used as a host for expression of acyl-ACP desaturases. For these studies, the coding sequence of wild type and mutant mature acyl-ACP desaturases were inserted into pLac3d. Cells were transformed with the resulting plasmid constructs and were then grown on plates or in liquid broth containing Luria-Bertani (LB) media with ampicillin (100 μg/ml), chloramphenicol (35 μg/ml), and kanamycin (40 μg/ml) selection. For non-selective growth, plates were supplemented with the fatty acid oleic acid solubilized in Tergitol NP-40 (Sigma) with final concentrations of 250 μg/ml oleic acid and 2% (v/v) Tergitol. Liquid broth was supplemented with oleic acid (solubilized in Tergitol NP-40) at a final concentration of 100 μg/ml. Oleic acid was initially prepared as 1000x stock solution in ethanol and solubilized in melted Tergitol, prior to addition to the media. Media used to test for complementation did not contain added oleic acid, and isopropyl-β-D-thiogalactoside (IPTG) was added at a concentration of 0.4 mM to induce expression of acyl-ACP desaturase.

Transformation. Transformation was conducted by electroporation using a 50 μl aliquot of competent MH13 cells harboring pACYC/LacAnFd and 0.1 to 0.5 μg of expression plasmid for a given acyl-ACP desaturase. Following electroporation, cells were resuspended in 500 μl of LB media and shaken (250 rpm) at 37° C. for 45 min to 1 h. Cells were then plated on media as described above. Alternatively, a 75 μl aliquot of the transformed cells was added to 25 ml of LB media containing IPTG and antibiotics at concentrations described above. These cells were then maintained with shaking at 30° or 37° C.

Electrocompetent MH13 (pACYC/LacAnFd) were prepared by growing a culture from a single colony in low-salt LB media (10 mg/ml Bacto tryptone, 5 mg/ml yeast extract, and 5 mg/ml sodium chloride) containing kanamycin (40 μg/ml) and chloramphenicol (35 μg/ml) and supplemented with oleic acid (100 μg/ml) and 2% Tergitol (v/v). Cells were prepared for transformation and electroporated as described in the BioRad protocol for high efficiency electro-transformation of *E. coli*.

Mutagenesis. Two methods were used for mutagenesis. The first, site directed mutagenesis, randomized a target residue at a specific location in the amino acid sequence of the castor $\Delta^9$-18:0-ACP desaturase. Four target residues were chosen: Met 114, Leu 118, Pro 179, and Gly 188. PCR was used to generate four populations of DNA. Each population consisted of sequences encoding castor $\Delta^9$-18:0-ACP desaturase with a randomized codon for residue 114, 118, 179, or 188. Each of the four populations was generated using PCR site directed mutagenesis to produce DNA products having equimolar proportions of each of the four nucleotides at each position of the target codon. For each of the four randomized products, an oligonucleotide primer was synthesized which hybridized to sequences adjacent to the target codon, and contained a randomized codon in place of the target codon sequences, the primer population containing equimolar proportions of each of the four nucleotides G, A, T, and C at the three positions within the replacement codon. This primer was used in conjunction with a primer homologous to the 5' terminus of the gene to amplify the gene segment between the two primer binding sites. A second overlapping fragment was then synthesized using PCR to amplify the remainder of the respective coding sequences of the four PCR reaction products. The fragments were then incorporated into larger gene fragments using overlap extension polymerase chain reaction (Ho et al., (1989) Gene 77:51-59). The gene fragments containing the randomized target codons were inserted into pLac3.

In the second mutagenesis method random mutations were introduced into the coding region sequence by digesting the castor $\Delta^9$-18:0-ACP desaturase coding region with DNase, and reassembling using PCR (W. P. Stemmer, (1994) Proc. Natl. Acad. Sci. USA 91:10747-10751). The entire coding region was reinserted into pLac3 to make a library of pLac3 castor $\Delta^9$-18:0-ACP desaturase genes with random mutations throughout the coding region.

Section II: Comparison of Combinatorial Full Positional Randomization with Other Methods Single Position Mutagenesis Four amino acid positions in the castor $\Delta^9$-18:0-ACP desaturase were identified by structural analysis (deductive reasoning by examination of a crystal structural model) as likely to participate in substrate specificity: 114, 118, 179, and 188. Independently, five positions were identified by random mutagenesis as likely to participate in substrate specificity: 114, 118, 179, 117, and 181. Together, this yielded a total of six positions identified as likely to participate in substrate specificity: 114, 117, 118, 19, 181, 188. To identify which of the 20 possible amino acids inserted at a target position would produce a mutant with the highest activity on 14 and 16 carbon substrates, libraries of mutants were generated by randomization of one of these positions at a time (single point randomization). Randomization resulted in substitution of each one of all 20 possible amino acids at the target position. Six libraries were generated, one for each target position. These libraries were introduced into MH13 bacteria to select for mutants with enhanced substrate specificities of 14 or 16 carbon chain length. Complementation of MH13, the unsaturated fatty acid auxotroph of E. coli, requires that the desaturase have a substrate specificity for 14 or 16 carbon chain length (or perhaps fewer) fatty acids. Recipient colonies which were able to grow under selective conditions were isolated. The mutant desaturase was purified from a crude lysate of a culture of the colony, and the specific activities for 14 and 16 carbon chain length substrates were determined for selected mutants by assay of the protein. For some mutants the specific activities of the enzyme were determined for 14, 16 and 18 carbon chain length fatty acyl ACP substrates.

Mutants produced from the two types of mutagenesis (random and single point randomization) were identified and compared. Table 2 lists the most active mutants identified by the two methods. Table 3 compares the activities of mutants at position 117 and mutants at position 181, which were identified using both methods of mutagenesis. Mutants identified from the libraries of target position randomized mutants (single point randomization) demonstrated the higher specific activities for 14 and 16 carbon substrates than did the mutants which were identified by random mutagenesis. Selection of mutants from a library produced by random mutagenesis only once produced the same, most active mutant identified by the full positional randomization method (L118F). Other selected mutants which resulted from random mutagenesis had catalytic rates inferior to the rates of mutants produced by single point randomization. The reason for this is that the random mutagenic process used could only generate between 4 and 7 amino acid substitutions per position. With respect to the six positions, at five of the positions, when offered all 19 substitutions by full randomization, a mutant enzyme with higher specific activity was obtained, and in the sixth case an identical enzyme having equivalent activity was obtained by both methods. This demonstrated that the greater number of substitutions tested for a single position facilitated an increased probability of a higher increase in specific activity for a particular substrate.

TABLE 2

| | | Random Mutagenesis[1] (RM) | | | | Single Point Randomization[2] (SPR) | | |
|---|---|---|---|---|---|---|---|---|
| | | Act[3] (nM/min./mg) | | | | Act[3] (nM/min./mg) | | |
| Site[4] | Sub[5] | 14 | 16 | 18 | Sub[5] | 14 | 16 | 18 |
| Met 114 | Ile | 3 | 22 | 260 | Ile | 3 | 22 | 260 |
| Met 114 | | | | | Phe/Tyr[6] | 5 | 0.8 | 7 |
| Thr 117 | Ile | 0.7 | 5 | 35 | Arg[6] | 3 | 30 | 332 |
| Leu 118 | Phe | 0.5 | 42 | 270 | Phe | 0.5 | 42 | 270 |
| Pro 179 | Leu | 15 | 22 | 206 | Ile[6] | 18 | 78 | 270 |
| Thr 181 | Ile | 0.7 | 5 | 196 | Phe[6] | 5 | 64 | 198 |
| Gly 188 | None Identified | | | | Leu[6] | 11 | 173 | 19 |

Key:
[1] Random point mutagenesis of the castor $\Delta^9$-18:0-ACP desaturase.
[2] Single point randomization using a primer encoding NNK to give 32-fold degeneracy with codons encoding all 20 amino acids.
[3] Specific activity measured using $^{14}$C-argentation thin layer chromatography assay in conjunction with phosphor imaging quantitation.
[4] Site of the amino acid position with respect to the mature castor open reading frame see following sheet for number definition.
[5] Substituted amino acid, in standard three letter format.
[6] Underlined amino acids identify substitutions that were not attainable by random mutagenesis.

Combinatorial Full Positional Randomization

In an effort to produce a mutant desaturase protein which had enhanced activity for 14 and 16 carbon substrates, a library of mutants were generated by randomizing all six candidate positions, 114, 117, 118, 179, 179, and 188, simultaneously. This procedure is termed combinatorial full positional randomization. The library was introduced into MH13, which were then plated on selective (unsupplemented) media. A sample set of 19 colonies which grew on the selective media were picked. The plasmid DNA was isolated from each colony and used to re-transform the MH13 to confirm that the plasmids encoded a modified desaturase. Plasmids from each of the selected colonies were purified and the DNA sequence of each selected mutant encoded was determined.

TABLE 3

| | | | Act[1] (nM/min./mg) | | |
|---|---|---|---|---|---|
| Site[2] | Method | Sub | 14 | 16 | 18 |
| Wt | | None | 0.8 | 12 | 820 |
| Thr 117 | RM[3] | Ile | 0.7 | 5 | 35 |
| | SPR[4] | Arg[5] | 3 | 30 | 332 |
| | SPR | Val | 1 | 0.7 | 35 |
| | SPR | Lys | 3 | 2.6 | 93 |
| Thr 181 | RM | Ile | 0.7 | 5 | 196 |
| | SPR | Phe | 5 | 64 | 198 |
| | SPR | Trp | 25 | 27 | 12 |

TABLE 3-continued

| Site[2] | Method | Sub | Act[1] (nM/min./mg) | | |
|---|---|---|---|---|---|
| | | | 14 | 16 | 18 |
| | SPR | Leu | 2.4 | 42 | 181 |
| | SPR | Met | 3 | 15 | 479 |

Key:
[1]Specific activity measured using $^{14}$C-argentation thin layer chromatography assay in conjunction with phosphor imaging quantitation.
[2]Site of the amino acid position with respect to the mature castor open reading frame see following sheet for number definition.
[3]RM: randomized mutagenesis of the castor $\Delta^9$-18:0-ACP desaturase
[4]SPR: Single Point Randomization (using a primer encoding NNK to give 32-fold degeneracy with codons encoding all 20 amino acids).
[5]underlined amino acids identify substitutions that were not attainable by random mutagenesis.

Conceptual translation of the DNA sequences indicated that all 19 mutants had distinct combinations of amino acids at the six candidate positions. All 19 mutant desaturase enzymes were produced and purified and subjected to in vitro enzyme assays. Table 4 lists six of the mutants produced and their specific activities for the different substrates.

TABLE 4

Combinatorial Mutants Containing T117R

| | Position | | | | | Activity[1] | | |
|---|---|---|---|---|---|---|---|---|
| | 114 | 117 | 118 | 179 | 181 | 188 | 14 | 16 | 18 |
| Wild Type | M | T | L | P | T | G | 0.8 | 11.5 | 820 |
| Mutants | | | | | | | | | |
| com2 | A | R | G | V | V | L | 59 | 270 | 420 |
| com3 | Q | R | P | V | D | L | 0 | 13 | 3 |
| com4 | T | R | A | L | S | L | 13 | 132 | 12 |
| com9 | V | R | G | S | C | L | 1.9 | 42 | nd[2] |
| com10 | Y | R | P | A | F | L | 2 | 22 | nd[2] |
| com25 | S | R | C | L | T | T | 100 | 390 | nd[2] |

[1]Activity (nm/min/mg) determined with 3 fatty acid ACP substrates
[2]nd = not determined The mutant having the consistently highest in vitro specific activities for the tested substrates was com2. As noted above, the in vitro activity of com25 was highly variable, and the values reported here represent the average. Despite the variability of the in vitro activity of com25, its in vivo activity in transgenic plants was consistent and surprisingly high. The transgenic plants expressing com25 produced more 16:0 fatty acid than did those expressing com2. Both com2 and com25, in vitro, had far higher specific activities for 14 and 16 carbon substrates than did any of the single position mutants (Table 5).

TABLE 5

Comparison of Combinatorial Full Positional Randomization with Other Methods[1]

| Position | SPR | 14 | 16 | RM | 14 | 16 |
|---|---|---|---|---|---|---|
| M114 | Phe | 6 | 0.1 | Ile | 4 | 2 |
| T117 | Arg | 4 | 3 | Leu | 1 | 0.5 |
| L118 | Phe | 1 | 4 | Phe | 1 | 4 |
| P179 | Ile | 23 | 7 | Leu | 19 | 2 |
| T181 | Trp | 31 | 2 | Leu | 1 | 4 |
| G188 | Leu | 14 | 15 | — | — | — |

TABLE 5-continued

Comparison of Combinatorial Full Positional Randomization with Other Methods[1]

| Position | SPR | 14 | 16 | RM | 14 | 16 |
|---|---|---|---|---|---|---|
| Com2* | | 74 | 23 | | | |
| Com25* | | 125 | 34 | | | |

[1]All activities are reported as the fold change in activity compared to the wild type castor $\Delta^9$-18:0-ACP desaturase activity for that chain length (i.e., 0.8 and 11.5 nm/min/mg protein for 14 and 16 carbon atom substrates, respectively).
Underlined residues are those yielding the highest increase when tested for activity in single point randomized mutants.
*Com2 M114A T117R L118G P179V T181V G188L
*Com25 M114S T117R L118C P179L T181T G188T Two of the amino acid substitutions in com2, T117R, and G188L, were determined to be the optimal substitutions for those positions by the independent single point randomization studies described above. This correlation indicates that the increase in specificity of the com2 mutant is due to the substitutions at these two residues in combination with the particular changes in the four other amino acid residues. Notably, neither of these changes were available via random mutagenesis. As indicated in Table 4, five of the 19 combinatorial mutants analyzed contained these two specific mutations, T117R and G188L, but contained different substitutions at the other four positions. These five mutants exhibited various changes in specific activity for the two substrates. Thus substitutions at positions 114, 118, 179 and 181 had a profound effect on the influence of the changes at positions 117 and 188. This is particularly notable when one compares the mutations in com2 versus those of com25 where a profound effect of substitutions in positions other than 117 is apparent. Therefore, the combination of substitutions at the other five sites could either accentuate the positive effects that T117R alone and T177R in combination with G188L have on activity, or alternatively, could reverse the effect.

Increasing the number of possible combinations of amino acids at all positions identified as affecting the substrate specificity (e.g. when substituted individually), including amino acid substitutions which are sub-optimal for affecting the substrate specificity individually, yields mutants with optimal activities.

Indeed, the accommodation of mutations which produce positive changes without in turn causing negative changes is likely of great importance for obtaining optimal performance. One could, in a sense, look at amino acids as molecular shims in the structure, the more shims of different sizes and properties that can be used to modulate the structure, the higher the likelihood that any particular structure will have optimal activity. Thus the approach of identifying as many positions as possible which might affect a particular property of the protein, and then presenting as many combinations at each of those positions as possible, coupled with an appropriate screening process, will identify a mutant protein which has optimal activity.

For the positions mutated in this example, random point mutagenesis could result in a limited number of amino acid substitutions: 6 at M114; 5 at T117; 5 at L118; 6 at P179; 6 at T181; and 5 at G188. Thus the total possible number of unique mutants obtainable through random point mutagenesis would be $6^3 \times 5^3 = 27,000$ unique mutants. If all 20 combinations were permissible as in the combinatorial full positional randomization method, that number would rise to $19^6 = 47,045,881$, or 1742-fold more combinations from which to select the optimal mutant for the particular trait. Since subtle changes can dramatically affect the activity of a protein, methods which result in more rather than fewer mutations of positions of amino acids shown to affect catalytic rates, will always produce equal or superior results to methods employing the more restrictive point mutagenesis.

Materials and Methods For Section II

Methods in this Section are the same as those used for Section I, unless as otherwise described below.

Single Point Randomization. Castor-$\Delta^9$-18:0-ACP desaturase was subjected to mutagenesis prior to introduction into the MH13 cells. PCR was used in site directed mutagenesis to randomize the three residues comprising a codon corresponding to a specified residue in the amino acid sequence of the castor $\Delta^9$-18:0-ACP desaturase. Target codons corresponding to Met 114, Thr 117, Leu 118, Pro 179, Thr 181 and Gly 188 were each subjected to independent randomization. Because these residues are located adjacent to the substrate-binding cavity, amino acid substitutions at these positions are considered highly likely to affect substrate specificity. These mutagenesis reactions yielded four populations, each one comprising a library of coding sequences with substitution mutations consisting of all 20 potential amino acids at the designated mutation site. An example for the introduction of all possible amino acid substitutions at position 117 by overlap extension PCR is diagrammed in FIG. 2. Primers used were 1: GTGAGCGGATAA-CAATTTCACACAGTCTAGAAAT (SEQ ID NO: 3), sequence flanking the unique XbaI site at the 5' end of the open reading frame; 2: CCAAATTGCCCAAGACGTCG-GACTTGCACCTGTTTCATCCCGAACTC-CATCCAAMNNATT CAGCATTGTTTG (SEQ ID NO: 4), the noncoding mutagenic oligonucleotide for position 117; 3: GAAACAGGTGCAAGTCCGACGTCTTGGGCAA (SEQ ID NO: 5), a non-mutagenic coding strand primer with overlap to the mutagenic 117 primer; 4: GTTTTCTGTC-CGCGGATCCATTCCTG (SEQ ID NO: 6), a noncoding strand primer flanking the unique SacII site of the open reading frame. A PCR fragment was generated by overlap extension of fragments a and b using primers 1 and 4. This fragment was restricted by XbaI and SacII and introduced into the equivalent sites into pLac3 containing the wild type castor $\Delta^9$-18:0-desaturase. The other five positions of castor $\Delta^9$-18:0-desaturase were mutated independently in an equivalent fashion to methods used for position 117.

Random mutagenesis. Random mutagenesis was performed on sequences encoding castor $\Delta^9$-18:0-ACP desaturase by single gene DNA shuffling (W. P. Stemmer, (1994)). The open reading frame was first amplified by PCR using the primers: GTGAGCGGATAACAATTTCACA-CAGTCTAGAAAT (SEQ ID NO: 7) which corresponds to the coding strand, and CACGAGGCCCTTTCGTCTTCAA-GAATTCTC (SEQ ID NO: 8) which corresponds to the noncoding strand. Approximately 50-200 bp from the wild type castor open reading frame was digested with DNaseI to make fragments at random positions within the open reading frame. The gene was then assembled by primerless PCR, followed by amplification of the full open reading frame using 5' and 3' specific primers. This method incorporated primarily point mutations at high frequency. The mutagenesis method used here was arbitrarily chosen, any method of point mutagenesis could have been used to produce equivalent results.

Figure 3:
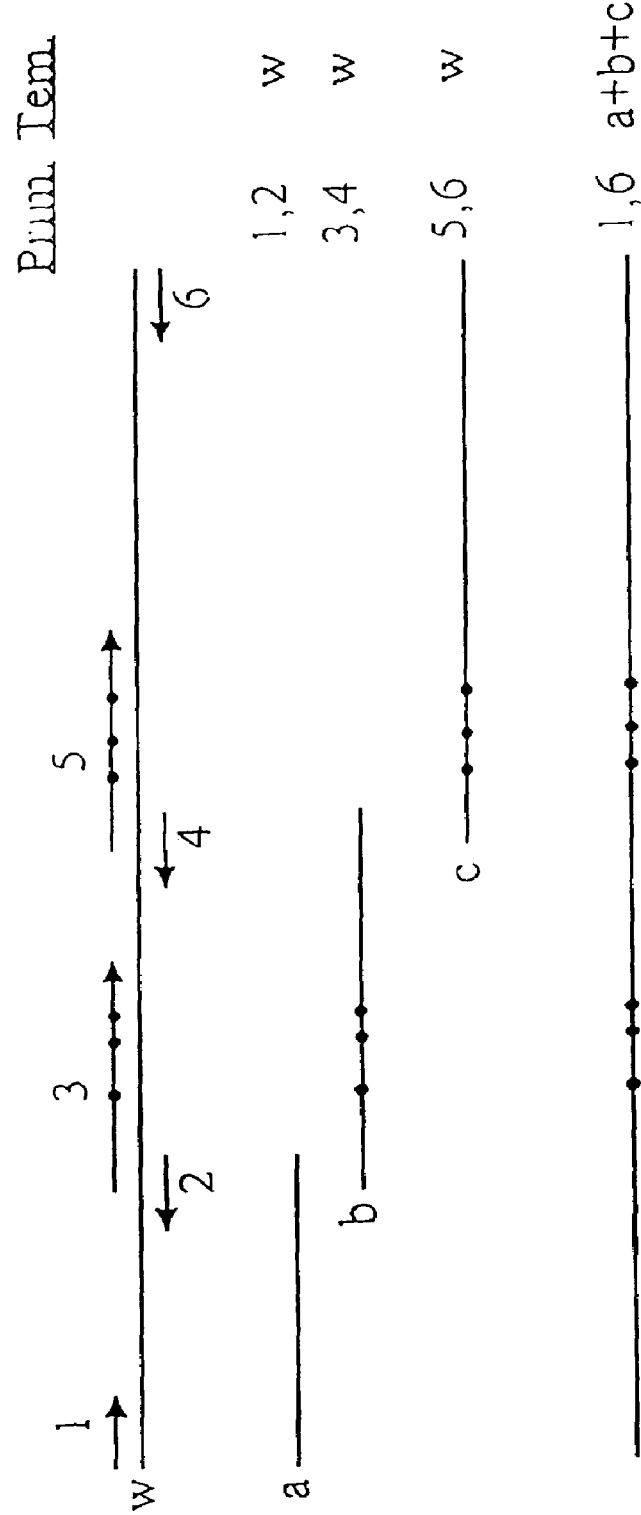
FIG. 3 is a diagram illustrating the primers used for the generation of a combinatorial library of castor $\Delta^9$-18:0-ACP desaturase with full positional randomization of positions 114, 117, 118, 179, 181, and 188.

Combinatorial full positional randomization. For the combinatorial 6 site-specific full positional randomization primers were engineered to contain NNK (where N refers to an equimolar mixture of G, A, T and C, and K refers to an equimolar mixture of G and T) for each of the six target codons. The full open reading frame was assembled and amplified by overlap extension PCR as shown in FIG. 3. Primers corresponding to the diagram were 1: GTGAGCG-GATAACAATTTCACACAGTCTAGAAAT (SEQ ID NO: 3), sequence flanking the unique XbaI site at the 5' end of the open reading frame; 2: TTGATAAGTGGGAAGGGCT-TCTTCCGTT (SEQ ID NO: 9), non-mutagenic noncoding primer; 3: AACGGAAGAAGCCCTTCCCACTTAT-CAAACANNKCTGAATNNKNNKGATG-GAGTTCGGGA TGAAAC (SEQ ID NO: 10), mutagenic coding strand primer; 4: TCCATTCCTGAACCAAT-CAAATATTG (SEQ ID NO: 11), non-mutagenic noncoding strand primer; 5: TTGATTGGTTCAGGAATGGATNN-KCGGNNKGAAAACAGTCCATACCTTNN-KTTCATCTAT ACATCATTCC (SEQ ID NO: 12), mutagenic coding strand primer; 6: GCAAAAGC-CAAAACGGTACCATCAGGATCA (SEQ ID NO: 13), noncoding non-mutagenic primer flanking the KpnI site. The three fragments were first amplified as shown in FIG. 3. They were isolated and amplified by overlap-extension PCR as described above for full positional randomization of T117. The final fragment was restricted using XbaI and KpnI, and introduced into the equivalent sites in pLac3 containing the wild type castor $\Delta^9$-18:0-ACP desaturase.

Selection of mutant desaturases with altered chain length specificity. To facilitate determination of the function of a plant acyl-ACP desaturase in E. coli, an expression vector containing the gene for plant-type ferredoxin, the redox partner of the plant desaturase, was transformed into the MH13 E. coli and maintained under selective pressure. These cells, MH13(pACYC/LacAnFd) were used in the following experiments. MH13(pACYC/LacAnFd) were transformed with the resulting libraries of mutated 18:0-ACP desaturase under conditions appropriate for expression. To achieve this, clones were restricted with either XbaI and KpnI, or XbaI and EcoRI, and introduced into the corresponding sites of plasmid pLac3 containing the mature castor $\Delta^9$-desaturase open reading frame. The plasmid pLac contains the Lac promoter which can be induced using the chemical inducer (IPTG). Selection media lacking unsaturated fatty acids was used to identify mutants with the ability to complement the unsaturated fatty acid auxotrophy. To confer survival under the selective conditions, a mutant desaturase would necessarily have an altered substrate chain length specificity of 16, 14 or fewer carbons. The selection for site directed mutants was performed in either liquid media or on agar plates. The selection for randomly generated mutants was performed on agar plates. Growth in liquid media involved several rounds of dilution and re-growth to enrich for mutations that resulted in the best complementation. DNA for all mutants identified in this fashion was isolated and reintroduced into the mutant E. coli cell strain, which was subjected to another round of selection to confirm the phenotype. The DNA of the selected desaturases were sequenced and translated conceptually to identify the specific mutations incurred.

Enzyme analyses. For determination of biochemical parameters of the desaturase mutants, the open reading frame was excised by restriction with XbaI and KpnI and ligated into the corresponding sites of the plasmid pLac3, which put the mature castor $\Delta^9$-desaturase open reading frame under the control of the Lac promoter. The plasmid was expressed in the cell line BL21(DE3) Gold (Novagen) for expression. Cells were grown to 0.5 OD600, induced by addition of 0.4 mM IPTG and harvested after four hours. The desaturase enzyme was extracted and purified to near homogeneity (90%) by HPLC cation exchange chromatography using Poros 20CM media (Perseptive Biosystems). Purified desaturase was assayed using C1-$^{14}$C acyl-ACP of appropriate chain lengths. Substrate and products were converted to methyl esters and analyzed by argentation thin layer chromatography and phoshor-imaging. Specific activities with the different substrates were calculated (Cahoon et al., (1997)).

Plant Transformation Methods

Plasmid Construction: A common transit peptide coding sequence (fragment "A") was amplified from a castor genomic clone using oligonucleotides: 5'-CCA AAA GAA AAA GGT AAG AAA ACC CGG GAT GGC TCT CAA GCT CAA TCC TTT CCT TTC TC-3' (SEQ ID NO: 14) and 5'-TTG CTC TCT CCC TGA GTT CCC TGA CTT GCT C-3' (SEQ ID NO: 15).

Internal fragments ("B" and "C", respectively) were amplified from com2 and com25 templates using oligonucleotides: 5'-GAG CAA GTC AGG GAA CTC AGG GAG AGA GCA A-3' (SEQ ID NO: 16) and 5'-TCC TTT GAC CTT CCT TGG GCT CTC TCT TCC AGC CTT CT-3' (SEQ ID NO: 17).

A common C-terminal coding sequence (fragment "D") ws amplified from a com2 template using oligonucleotides: 5'-GAA GGC TGG AAG AGA GAG CCC AAG GAA GGG CAA AGG A-3' (SEQ ID NO: 18) and 5'-TGA ATT CGA TAT CGA GCT CTA CAG CTT CAC TTG CCT ATC GAA-3' (SEQ ID NO: 19).

Fragments B and C were independently combined with a mixture of fragments A and D for use as templates in PCR reactions with primers SEQ ID NO: 14 and SEQ ID NO: 19.

The resulting PCR products were then used as templates for further PCR reactions with primers: 5'-GCG GAT CCT TAA TTA ATG GCT CTC AAG CTC AAT CC-3' (SEQ ID NO: 20) and 5'-CCG CTC GAG GCG CGC CTA CAG CTT CAC TTG CCT ATC G-3' (SEQ ID NO: 21). The resulting PCR products were then digested with PacI and AscI and inserted into the transformation vector pBBV-PHAS to create pPHAS-com2 and pPHAS-com25.

Plant material and growth conditions: *Arabidopsis* fab1 fae1 double mutant plants were grown at 20° C. under continuous light (90 to 120 E m$^{-2}$ sec$^{-1}$ PAR). To construct the fab1 fae1 double mutant, fab1 mutant flowers were pollinated with fae1 pollen. Fab1 fae1 double mutant individuals in the F2 generation were identified based on the production of seed accumulating more than 20% palmitic acid combined with the inability to accumulate fatty acids greater than 18 carbons in length.

Plant transformation: *Agrobacterium tumefaciens* strain GV3101 was transformed with pPHAS-com2 and pPHAS-com25. *Arabidopsis* fab1 fae1 double mutant plants were transformed with the mutant desaturases according to the floral dip method of Clough and Bent (Plant J. 16:735-743 (1998)).

Accumulation of 16:1 and 18:1 unsaturated fatty acids: Seeds from 32 com2-transformed individual lines and 22 com25-transformed individual lines were examined for percentage of unsaturated fatty acids 16:1 and 18:1. The percentage of 16:1 varied from approximately 5% to as high as about 22% in both the com2 and the com25 lines. However, 73% of the tested com25 lines (16 out of 22) had 16:1 fatty acid at 15% or higher whereas only 25% of the com2 lines (7-8/32) had 15% or more of their fatty acid in the 16:1 form.

---

SEQUENCE LISTING

```
<160> NUMBER OF SEQ ID NOS: 19

<210> SEQ ID NO 1
<211> LENGTH: 363
<212> TYPE: PRT
<213> ORGANISM: Ricinus communis
<220> FEATURE:
<221> NAME/KEY: misc_feature
<223> OTHER INFORMATION: ricinus communis delta 9 18:0 Acyl ACP
      Desaturase

<400> SEQUENCE: 1

Ala Ser Thr Leu Lys Ser Gly Ser Lys Glu Val Glu Asn Leu Lys Lys
1               5                   10                  15

Pro Phe Met Pro Pro Arg Glu Val His Val Gln Val Thr His Ser Met
                20                  25                  30

Pro Pro Gln Lys Ile Glu Ile Phe Lys Ser Leu Asp Asn Trp Ala Glu
            35                  40                  45

Glu Asn Ile Leu Val His Leu Lys Pro Val Glu Lys Cys Trp Gln Pro
        50                  55                  60

Gln Asp Phe Leu Pro Asp Pro Ala Ser Asp Gly Phe Asp Glu Gln Val
65                  70                  75                  80

Arg Glu Leu Arg Glu Arg Ala Lys Glu Ile Pro Asp Asp Tyr Phe Val
                85                  90                  95

Val Leu Val Gly Asp Met Ile Thr Glu Glu Ala Leu Pro Thr Tyr Gln
            100                 105                 110
```

Thr Met Leu Asn Thr Leu Asp Gly Val Arg Asp Glu Thr Gly Ala Ser
            115                 120                 125

Pro Thr Ser Trp Ala Ile Trp Thr Arg Ala Trp Thr Ala Glu Glu Asn
    130                 135                 140

Arg His Gly Asp Leu Leu Asn Lys Tyr Leu Tyr Leu Ser Gly Arg Val
145                 150                 155                 160

Asp Met Arg Gln Ile Glu Lys Thr Ile Gln Tyr Leu Ile Gly Ser Gly
                165                 170                 175

Met Asp Pro Arg Thr Glu Asn Ser Pro Tyr Leu Gly Phe Ile Tyr Thr
            180                 185                 190

Ser Phe Gln Glu Arg Ala Thr Phe Ile Ser His Gly Asn Thr Ala Arg
        195                 200                 205

Gln Ala Lys Glu His Gly Asp Ile Lys Leu Ala Gln Ile Cys Gly Thr
    210                 215                 220

Ile Ala Ala Asp Glu Lys Arg His Glu Thr Ala Tyr Thr Lys Ile Val
225                 230                 235                 240

Glu Lys Leu Phe Glu Ile Asp Pro Asp Gly Thr Val Leu Ala Phe Ala
                245                 250                 255

Asp Met Met Arg Lys Lys Ile Ser Met Pro Ala His Leu Met Tyr Asp
            260                 265                 270

Gly Arg Asp Asp Asn Leu Phe Asp His Phe Ser Ala Val Ala Gln Arg
        275                 280                 285

Leu Gly Val Tyr Thr Ala Lys Asp Tyr Ala Asp Ile Leu Glu Phe Leu
    290                 295                 300

Val Gly Arg Trp Lys Val Asp Lys Leu Thr Gly Leu Ser Ala Glu Gly
305                 310                 315                 320

Gln Lys Ala Gln Asp Tyr Val Cys Arg Leu Pro Pro Arg Ile Arg Arg
                325                 330                 335

Leu Glu Glu Arg Ala Gln Gly Arg Ala Lys Glu Ala Pro Thr Met Pro
            340                 345                 350

Phe Ser Trp Ile Phe Asp Arg Gln Val Lys Leu
        355                 360

<210> SEQ ID NO 2
<211> LENGTH: 1092
<212> TYPE: DNA
<213> ORGANISM: Ricinus communis
<220> FEATURE:
<221> NAME/KEY: misc_feature
<223> OTHER INFORMATION: residues 138 to 1239 of open reading frame

<400> SEQUENCE: 2
gcctctaccc tcaagtctgg ttctaaggaa gttgagaatc tcaagaagcc tttcatgcct     60
cctcgggagg tacatgttca ggttacccat tctatgccac cccaaaagat tgagatcttt    120
aaatccctag acaattgggc tgaggagaac attctggttc atctgaagcc agttgagaaa    180
tgttggcaac cgcaggattt tttgccagat cccgcctctg atggatttga tgagcaagtc    240
agggaactca gggagagagc aaaggagatt cctgatgatt attttgttgt tttggttgga    300
gacatgataa cggaagaagc ccttcccact tatcaaacaa tgctgaatac cttggatgga    360
gttcgggatg aaacaggtgc aagtcctact tcttgggcaa tttggacaag ggcatggact    420
gcggaagaga atagacatgg tgacctcctc aataagtatc tctacctatc tggacgagtg    480
gacatgaggc aaattgagaa gacaattcaa tatttgattg gttcaggaat ggatccacgg    540
acagaaaaca gtccataacct tgggttcatc tatacatcat tccaggaaag ggcaaccttc    600

```
atttctcatg ggaacactgc ccgacaagcc aaagagcatg gagacataaa gttggctcaa     660
atatgtggta caattgctgc agatgagaag cgccatgaga cagcctacac aaagatagtg     720
gaaaaactct ttgagattga tcctgatgga actgttttgg cttttgctga tatgatgaga     780
aagaaaattt ctatgcctgc acacttgatg tatgatggcc gagatgataa tcttttttgac    840 cacttttcag ctgttgcgca gcgtcttgga gtctacacag caaaggatta tgcagatata     900
ttggagttct tggtgggcag atggaaggtg gataaactaa cgggcctttc agctgaggga     960
caaaaggctc aggactatgt ttgtcggtta cctccaagaa ttagaaggct ggaagagaga    1020
gctcaaggaa gggcaaagga agcacccacc atgcctttca gctggatttt cgataggcaa   1080
gtgaagctgt ag                                                        1092

<210> SEQ ID NO 3
<211> LENGTH: 34
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer; sequence flanking unique XbaI site
      at the 5' end of the open reading frame

<400> SEQUENCE: 3
gtgagcggat aacaatttca cacagtctag aaat                                 34

<210> SEQ ID NO 4
<211> LENGTH: 72
<212> TYPE: DNA
<213> ORGANISM: Artificial
<220> FEATURE:
<223> OTHER INFORMATION: amplification primer
<220> FEATURE:
<221> NAME/KEY: misc_feature
<222> LOCATION: (56)..(57)
<223> OTHER INFORMATION: PCR primer is a degenerate oligonucleotide in
      which "n" indicates the presence of either C, A, T or G at that
      nucleotide position

<400> SEQUENCE: 4
ccaaattgcc caagacgtcg gacttgcacc tgtttcatcc cgaactccat ccaamnnatt      60
cagcattgtt tg                                                         72

<210> SEQ ID NO 5
<211> LENGTH: 31
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 5
gaaacaggtg caagtccgac gtcttgggca a                                    31

<210> SEQ ID NO 6
<211> LENGTH: 26
<212> TYPE: DNA
<213> ORGANISM: Artificial
<220> FEATURE:
<223> OTHER INFORMATION: amplification primer
<220> FEATURE:
<221> NAME/KEY: misc_feature
```

<223> OTHER INFORMATION: PCR primer

<400> SEQUENCE: 6
gttttctgtc cgcggatcca ttcctg                                    26

<210> SEQ ID NO 7
<211> LENGTH: 34
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 7
gtgagcggat aacaatttca cacagtctag aaat                           34

<210> SEQ ID NO 8
<211> LENGTH: 30
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 8
cacgaggccc tttcgtcttc aagaattctc                                30

<210> SEQ ID NO 9
<211> LENGTH: 28
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 9
ttgataagtg ggaagggctt cttccgtt                                  28

<210> SEQ ID NO 10
<211> LENGTH: 66
<212> TYPE: DNA
<213> ORGANISM: Artificial
<220> FEATURE:
<223> OTHER INFORMATION: amplification primer
<220> FEATURE:
<221> NAME/KEY: misc_feature
<222> LOCATION: (32)..(34)
<223> OTHER INFORMATION: PCR primer is degenerate olignucleotide in
      which "n" indicates the presence of either C, A T, or G at that
      nucleotide position and in which "k" indicates either T or G
<220> FEATURE:
<221> NAME/KEY: misc_feature
<222> LOCATION: (41)..(43)
<223> OTHER INFORMATION: PCR primer is a degenerate oligonucleotide in
      which "n" indicates the presence of either C, A, T or G and in
      which "k" indicates the presence of either T or G.
<220> FEATURE:
<221> NAME/KEY: misc_feature
<222> LOCATION: (44)..(46)
<223> OTHER INFORMATION: PCR primer is a degenerate oligonucleotide in
      which "n" indicates the presence of either C, A, T, or G at that
      nucleotide position and in which "k" indicates the presence of
      either T or G.

<400> SEQUENCE: 10
aacggaagaa gcccttccca cttatcaaac annkctgaat nnknnkgatg gagttcggga    60
tgaaac    66

<210> SEQ ID NO 11
<211> LENGTH: 26
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 11
tccattcctg aaccaatcaa atattg    26

<210> SEQ ID NO 12
<211> LENGTH: 70
<212> TYPE: DNA
<213> ORGANISM: Artificial
<220> FEATURE:
<223> OTHER INFORMATION: amplification primer
<220> FEATURE:
<221> NAME/KEY: misc_feature
<222> LOCATION: (22)..(24)
<223> OTHER INFORMATION: PCR primer in a degenerate oligonucleotide in
      which "n" indicates the presence of either C, A, T or G at that
      nucleotide position and in which "k" indicates the presence of
      either T or G at that nucleotide position.
<220> FEATURE:
<221> NAME/KEY: misc_feature
<222> LOCATION: (28)..(30)
<223> OTHER INFORMATION: PCR primer in a degenerate oligonucleotide in
      which "n" indicates the presence of either C, A, T or G at that
      nucleotide position and in which "k" indicates the presence of
      either T or G at that nucleotide position.
<220> FEATURE:
<221> NAME/KEY: misc_feature
<222> LOCATION: (49)..(51)
<223> OTHER INFORMATION: PCR primer in a degenerate oligonucleotide in
      which "n" indicates the presence of either C, A, T or G at that
      nucleotide position and in which "k" indicates the presence of
      either T or G at that nucleotide position.

<400> SEQUENCE: 12
ttgattggtt caggaatgga tnnkcggnnk gaaaacagtc catacctttnn kttcatctat    60 acatcattcc    70

<210> SEQ ID NO 13
<211> LENGTH: 30
<212> TYPE: DNA
<213> ORGANISM: Artificial
<220> FEATURE:
<223> OTHER INFORMATION: amplification primer
<220> FEATURE:
<221> NAME/KEY: misc_feature
<223> OTHER INFORMATION: PCR primer

<400> SEQUENCE: 13
gcaaaagcca aaacggtacc atcaggatca    30

<210> SEQ ID NO 14
<211> LENGTH: 59
<212> TYPE: DNA
<213> ORGANISM: artificial
<220> FEATURE:
<223> OTHER INFORMATION: amplification primer

<400> SEQUENCE: 14

```
ccaaaagaaa aaggtaagaa aacccgggat ggctctcaag ctcaatcctt tcctttctc        59

<210> SEQ ID NO 15
<211> LENGTH: 31
<212> TYPE: DNA
<213> ORGANISM: artificial
<220> FEATURE:
<223> OTHER INFORMATION: amplification primer

<400> SEQUENCE: 15
ttgctctctc cctgagttcc ctgacttgct c                                     31

<210> SEQ ID NO 16
<211> LENGTH: 31
<212> TYPE: DNA
<213> ORGANISM: artificial
<220> FEATURE:
<223> OTHER INFORMATION: amplification primer

<400> SEQUENCE: 16
gagcaagtca gggaactcag ggagagagca a                                     31

<210> SEQ ID NO 17
<211> LENGTH: 38
<212> TYPE: DNA
<213> ORGANISM: artificial
<220> FEATURE:
<223> OTHER INFORMATION: amplification primer

<400> SEQUENCE: 17
tcctttgacc ttccttgggc tctctcttcc agccttct                              38

<210> SEQ ID NO 18
<211> LENGTH: 37
<212> TYPE: DNA
<213> ORGANISM: artificial
<220> FEATURE:
<223> OTHER INFORMATION: amplification primer

<400> SEQUENCE: 18
gaaggctgga agagagagcc caaggaaggg caaagga                               37

<210> SEQ ID NO 19
<211> LENGTH: 42
<212> TYPE: DNA
<213> ORGANISM: artificial
<220> FEATURE:
<223> OTHER INFORMATION: amplification primer

<400> SEQUENCE: 19
tgaattcgat atcgagctct acagcttcac ttgcctatcg aa                         42
```

The invention claimed is:

1. A DNA expression construct comprising a nucleic acid sequence which encodes a mutant $\Delta^9$-18:0-ACP desaturase having one or more amino acid substitutions selected from the group consisting of:
   a) Ala, Thr, Ser, or Ile for Met 114 of SEQ ID NO: 1;
   b) Arg for Thr 117 of SEQ ID NO: 1;
   c) Gly, Ala or Cys for Leu 118 of SEQ ID NO: 1;
   d) Val or Leu for Pro 179 of SEQ ID NO: 1;
   e) Val, Ser, Phe or Trp for Thr 181 of SEQ ID NO: 1; and
   f) Leu or Thr for Gly 188 of SEQ ID NO: 1.

2. The DNA expression construct of claim 1 in which the nucleic acid sequence encodes each of the following amino acid substitutions:
   a) Ala for Met 114 of SEQ ID NO: 1;
   b) Arg for Thr 117 of SEQ ID NO: 1;
   c) Gly for Leu 118 of SEQ ID NO: 1;
   d) Val for Pro 179 of SEQ ID NO: 1;
   e) Val for Thr 181 of SEQ ID NO: 1; and
   f) Leu for Gly 188 of SEQ ID NO: 1.

3. The DNA expression construct of claim 1 in which the nucleic acid sequence encodes each of the following amino acid substitutions:

a) Thr for Met 114 of SEQ ID NO: 1;
b) Arg for Thr 117 of SEQ ID NO: 1;
c) Ala for Leu 118 of SEQ ID NO: 1;
d) Leu for Pro 179 of SEQ ID NO: 1;
e) Ser for Thr 181 of SEQ ID NO: 1; and
f) Leu for Gly 188 of SEQ ID NO: 1.

4. The DNA expression construct of claim 1 in which the nucleic acid sequence encodes each of the following amino acid substitutions:
a) Ser for Met 114 of SEQ ID NO: 1;
b) Arg for Thr 117 of SEQ ID NO: 1;
c) Cys for Leu 118 of SEQ ID NO: 1;
d) Leu for Pro 179 of SEQ ID NO: 1; and
e) Thr for Gly 188 of SEQ ID NO: 1.

5. The DNA expression construct of claim 1 in which the nucleic acid sequence encodes the amino acid substitutions Arg for Thr 117 and Leu for Gly 188, each of SEQ ID NO: 1.

6. The DNA expression construct of claim 1 in which the nucleic acid sequence encodes the amino acid substitution Arg for Thr 117 of SEQ ID NO: 1.

7. The DNA expression construct of claim 1 in which the nucleic acid sequence encodes the amino acid substitution Phe for Thr 181 of SEQ ID NO: 1.

8. The DNA expression construct of claim 1 in which the nucleic acid sequence encodes the amino acid substitution Trp for Thr 181 of SEQ ID NO: 1.

9. The DNA expression construct of claim 1 in which the nucleic acid sequence encodes the amino acid substitutions Ile for Met 114 and Leu for Gly 188 of SEQ ID NO: 1.

10. The DNA expression construct of any one of claims 1, 2, 3, 4, 5, 6, 7, 8, or 9 wherein the nucleic acid sequence is selected from the $\Delta^9$-18:0-ACP desaturase sequences from a member of the group consisting castor, brassica, sunflower, yellow lupine, cotton, coriander, maize, sesame, rice, flax, safflower, avocado and cucumber.

11. A DNA expression construct comprising a nucleic acid sequence which encodes a mutant $\Delta^9$-18:0-ACP desaturase selected from the group consisting of
a. a mutant having each of the following amino acid substitutions: Ala for Met 114; Arg for Thr 117; Gly for Leu 118; Val for Pro 179; Val for Thr 181 and Leu for Gly 188, all of SEQ ID NO: 1;
b. a mutant having each of the following amino acid substitutions: Thr for Met 114; Arg for Thr 117; Ala for Leu 118; Leu for Pro 179; Ser for Thr 181 and Leu for Gly 188, all of SEQ ID NO: 1;
c. a mutant having each of the following amino acid substitutions: Ser for Met 114; Arg for Thr 117; Cys for Leu 118; Leu for Pro 179; and Thr for Gly 188, all of SEQ ID NO: 1;
d. a mutant in which Arg is substituted for Thr 117 and Leu for Gly 188, each of SEQ ID NO: 1;
e. a mutant in which Ile is substituted for Met 114 and Leu is substituted for Gly 188, each of SEQ ID NO: 1;
f. a mutant in which Arg is substituted for Thr 117 of SEQ ID NO: 1;
g. a mutant in which Phe is substituted for Thr 181 of SEQ ID NO: 1; and
h. a mutant in which Trp is substituted for Thr 181 of SEQ ID NO: 1.

12. The DNA expression construct of claim 11 wherein the nucleic acid sequence is selected from the $\Delta^9$-18:0-ACP desaturase sequence from a member of the group consisting of castor, brassica, sunflower, yellow lupine, cotton, coriander, maize, sesame, rice, flax, safflower, avocado and cucumber.

13. A cell transformed with a DNA expression construct selected from the group consisting of the DNA expression constructs of claim 11.

14. The cell of claim 13 which is a prokaryotic cell.

15. The cell of claim 13 which is an eukaryotic cell.

16. The cell of claim 15 which is a plant cell.

17. A transgenic plant expressing a DNA construct selected from the group consisting of the DNA constructs of claim 11.

18. The transgenic plant of claim 17 which is *Arabidopsis thaliana*.

19. The transgenic plant of claim 18 which is selected from the group consisting of castor, brassica, sunflower, yellow lupine, cotton, coriander, maize, sesame, rice, flax, safflower, avocado and cucumber.

* * * * *